United States Patent
Tanner

[11] Patent Number: 6,145,509
[45] Date of Patent: Nov. 14, 2000

[54] DEPTH SENSOR DEVICE FOR USE IN A SURGICAL PROCEDURE

[75] Inventor: Howard Tanner, Logan, Utah

[73] Assignee: EVA Corporation, Bethesda, Md.

[21] Appl. No.: 09/342,044

[22] Filed: Jun. 28, 1999

Related U.S. Application Data

[60] Provisional application No. 60/093,985, Jul. 24, 1998.

[51] Int. Cl.[7] ................................................. A61B 19/00
[52] U.S. Cl. ............................................. 128/897; 606/13
[58] Field of Search .................................. 606/7, 10, 11, 606/12, 13, 14, 15, 16, 17, 2; 128/897, 898; 600/474

[56] References Cited

U.S. PATENT DOCUMENTS

| | | | |
|---|---|---|---|
| 4,905,698 | 3/1990 | Strohl, Jr. et al. | 600/424 |
| 5,099,845 | 3/1992 | Besz et al. | 600/424 |
| 5,196,006 | 3/1993 | Klopotek et al. | 606/10 |
| 5,325,873 | 7/1994 | Hirschi et al. | 600/424 |
| 5,425,367 | 6/1995 | Shapiro et al. | 600/424 |
| 5,435,724 | 7/1995 | Goodman et al. | 606/10 |
| 5,611,345 | 3/1997 | Hibbeln | 600/424 |
| 5,622,170 | 4/1997 | Schulz | 600/424 |
| 5,645,065 | 7/1997 | Shapiro et al. | 600/424 |
| 5,800,352 | 9/1998 | Ferre et al. | 128/897 |
| 5,803,089 | 9/1998 | Ferre et al. | 128/897 |
| 5,829,444 | 11/1998 | Ferre et al. | 128/897 |
| 5,846,189 | 12/1998 | Pincus | 128/897 |
| 5,879,297 | 3/1999 | Haynor et al. | 600/424 |
| 5,882,304 | 3/1999 | Ehnholm et al. | 600/424 |
| 5,899,860 | 5/1999 | Pfeiffer et al. | 600/424 |
| 6,009,878 | 1/2000 | Weijand et al. | 600/424 |

*Primary Examiner*—Samuel G. Gilbert
*Assistant Examiner*—Joseph A. Cadugan

[57] ABSTRACT

A depth sensor is disclosed for sensing the position of a surgical device within a vessel wall during a surgical procedure. The depth sensor includes a housing, sensing assembly for sensing acoustic wave information generated during the surgical procedure, a processing assembly for processing the acoustic wave information received from the sensing assembly and a control assembly that receives data from the processing assembly thereby enabling operational control of the penetration device.

11 Claims, 3 Drawing Sheets

DEPTH SENSOR DEVICE FOR USE IN A SURGICAL PROCEDURE

CROSS REFERENCE TO RELATED PATENT APPLICATION

This application relates to and claims priority on provisional application serial No. 60/093,985 filed Jul. 24, 1998 and entitled "Depth Gauge Device For Use In A Surgical Procedure."

FIELD OF THE INVENTION

The present invention relates generally to a depth sensor device for use during a surgical procedure. In particular, the present invention relates to a depth sensor device for use during a pulsed laser based surgical procedure that enables sensing and thereby the control of depth of penetration of various mammalian tissue by a penetration device.

BACKGROUND OF THE INVENTION

The inventor of the subject matter of the present invention is aware of no prior attempts to measure, in real time, the depth of penetration of mammalian tissue during a surgical procedure.

OBJECTS OF THE INVENTION

It is therefore an object of the present invention to provide a device that is capable of measuring strata-by-strata the depth to which mammalian tissue is penetrated during a surgical procedure by a penetration device.

It is another object of the present invention to provide a device that is capable of detecting the acoustic wave information created during the penetration of mammalian tissue during a surgical procedure.

It is another object of the present invention to provide a device that is capable of extrapolating particular acoustic wave signatures from the sensed acoustic wave information during penetration of mammalian tissue enabling the determination of the depth of penetration of the tissue by the penetration device.

It is another object of the present invention to provide a device that is capable of measuring and thereby controlling the depth to which mammalian tissue is penetrated by a penetration device during a surgical procedure.

It is another object of the present invention to provide a depth gauge device that is capable of measuring, in real time, the depth of penetration of the tissue by a penetration device.

SUMMARY OF THE INVENTION

The present invention is directed to a depth sensor for sensing the position of a penetration device within mammalian tissue during a surgical procedure. The depth sensor incorporates a housing, a sensing assembly, a processing assembly and a control assembly.

The sensing assembly preferably senses acoustic waves which are propagated by the penetration device as it penetrates tissue during a surgical procedure.

The processing assembly receives acoustic wave information from the sensing assembly and differentiates the unique acoustic signatures contained therein. Unique acoustic wave signatures are generated as the penetration device passes through the various strata of the involved tissue.

The control assembly receives information from the processing assembly which enables the determination, by comparison, with imbedded information, the depth to which the penetration device has penetrated the involved tissue thereby enabling its subsequent controlled advancement/withdrawal.

In a preferred embodiment, the control assembly determines the depth to which a penetration device will penetrate a vessel wall.

The depth sensor may further include an indicator assembly that indicates the depth of the penetration device within the subject tissue during a surgical procedure. The indicator assembly may provide an audible indication to a user of the depth of the device within the tissue sample; it may also provide a visual indication.

The control and indicator assemblies of the present invention, which connect directly to the laser fiber of the penetration device may also be remotely placed when using ultrasound (through skin) sensing technologies.

The depth sensor according to the present invention may be linked to the penetration device such that the operation of the penetration device is controlled in response to sensed acoustic wave information.

It is to be understood that both the foregoing general description and the following detailed description are exemplary and explanatory only, and are not restrictive of the invention, as claimed. The accompanying drawings, which are incorporated herein by reference, and which constitute a part of this specification, illustrate certain embodiments of the invention, and together with the detailed description serve to explain the principles of the present invention.

BRIEF DESCRIPTION OF THE DRAWINGS

The invention will be described in conjunction with the following drawings in which like reference numerals designate like elements and wherein.

DETAILED DESCRIPTION OF PREFERRED EMBODIMENTS

The present invention will be described in connection with the repair of an abdominal aortic aneurysm, whereby a repair graft is secured to the aneurysmal vessel wall thereby excluding the aneurysm from the circulatory system. As a part of the attachment process of the repair graft, a penetration assembly is used to repair the aneurysm, as disclosed in U.S. patent application Ser. No. 08/896,415, entitled "METHOD AND APPARATUS FOR THE SURGICAL REPAIR OF ANEURYSMS", filed on Jul. 18, 1997, the disclosure of which is incorporated herein by reference. The description of the present invention in connection with the repair of aneurysms is provided for example. It is not considered to limit the scope and use of the present invention. Rather, it is contemplated that the present invention may be used in connection with other intraluminal surgical procedures.

Figure 3:
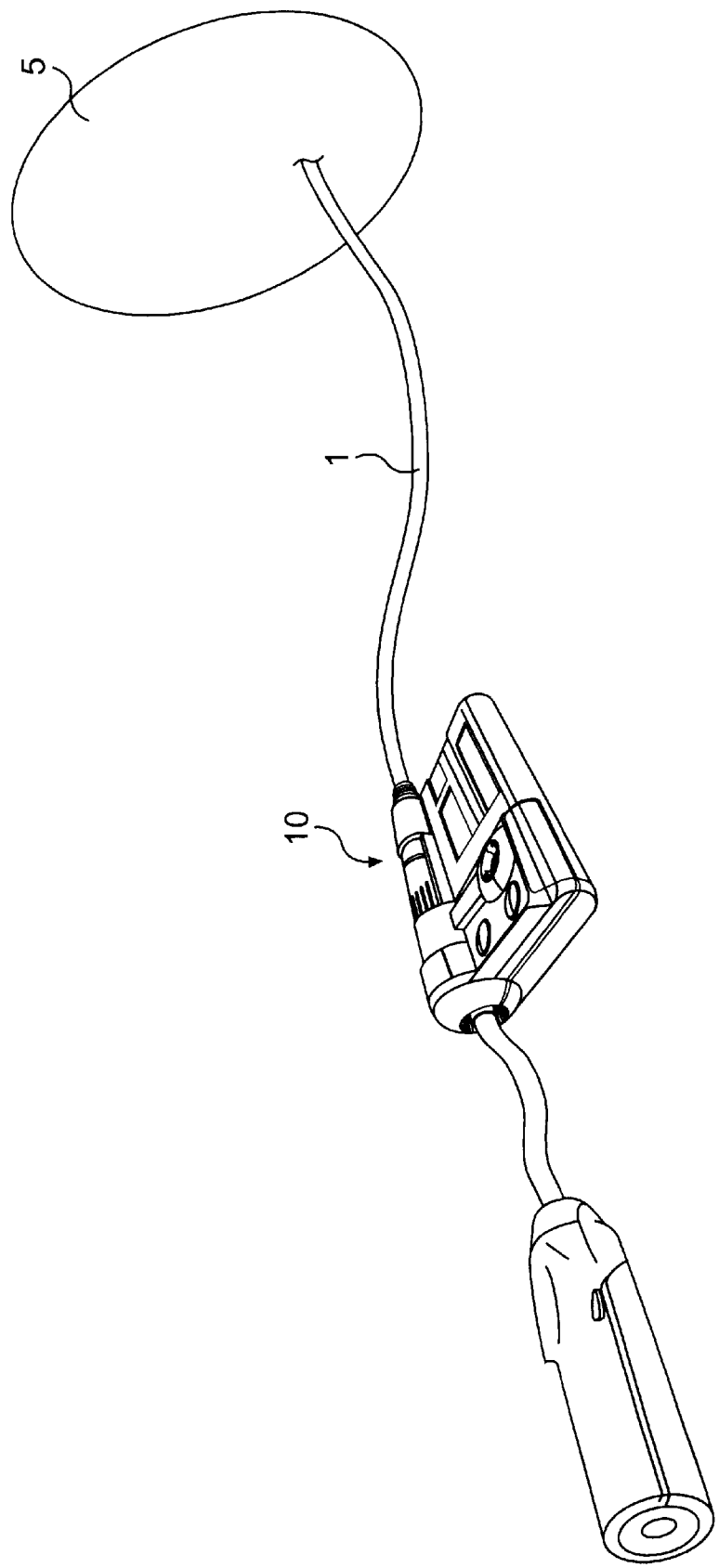
FIG. 3 is an illustration of the position sensor device of the present invention during a surgical procedure.

The depth sensor 10 includes a sensing assembly 120, a control assembly 130, and a processing assembly 140. As various layers of tissue are penetrated during a surgical procedure by the penetration device 1 that extends from a patient 5, as shown in FIG. 3, unique acoustic waves are generated with the penetration of each successive layer of tissue. The sensing assembly 120 senses acoustic wave information which are then transmitted to the processing assembly 140. The processing assembly 140 processes the acoustic wave information to differentiate one acoustic signature from another. The processing assembly 140 then transmits this information to the control assembly 130. The control assembly 130 then operates indicator assemblies, discussed below, to provide an indication of the depth of tissue penetration which enables the controlled operation of the penetration device by the surgeon. It is contemplated that the depth sensor 10 be directly linked to the penetration device 1 such that the operation of the penetration device 1 is automatically controlled by the depth sensor 10 in response to sensed acoustic wave information.

The sensing assembly 120 preferably includes a sensor that is capable of detecting acoustic waves which are generated as the penetration device penetrates the subject tissue. The sensing assembly 120 may include a transducer assembly for sensing acoustic waves generated during tissue penetration. The present invention, however, is not limited to a transducer assembly; rather, it is contemplated that other assemblies that are capable of sensing acoustic waves are considered to be well within the scope of the present invention.

Figure 1:
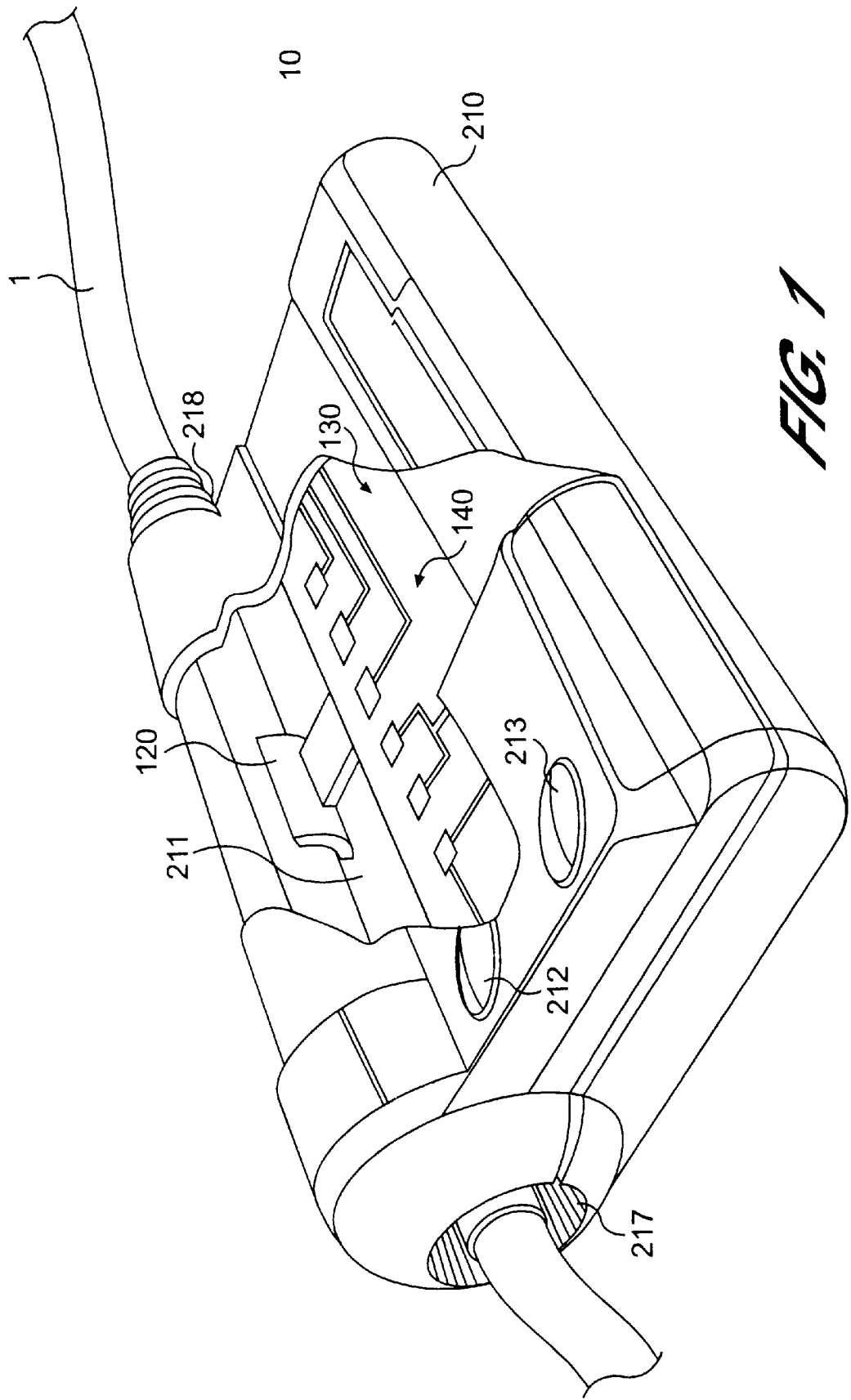
FIG. 1 is a partial cut-away perspective view of the position sensor according to the present invention.
Figure 2:
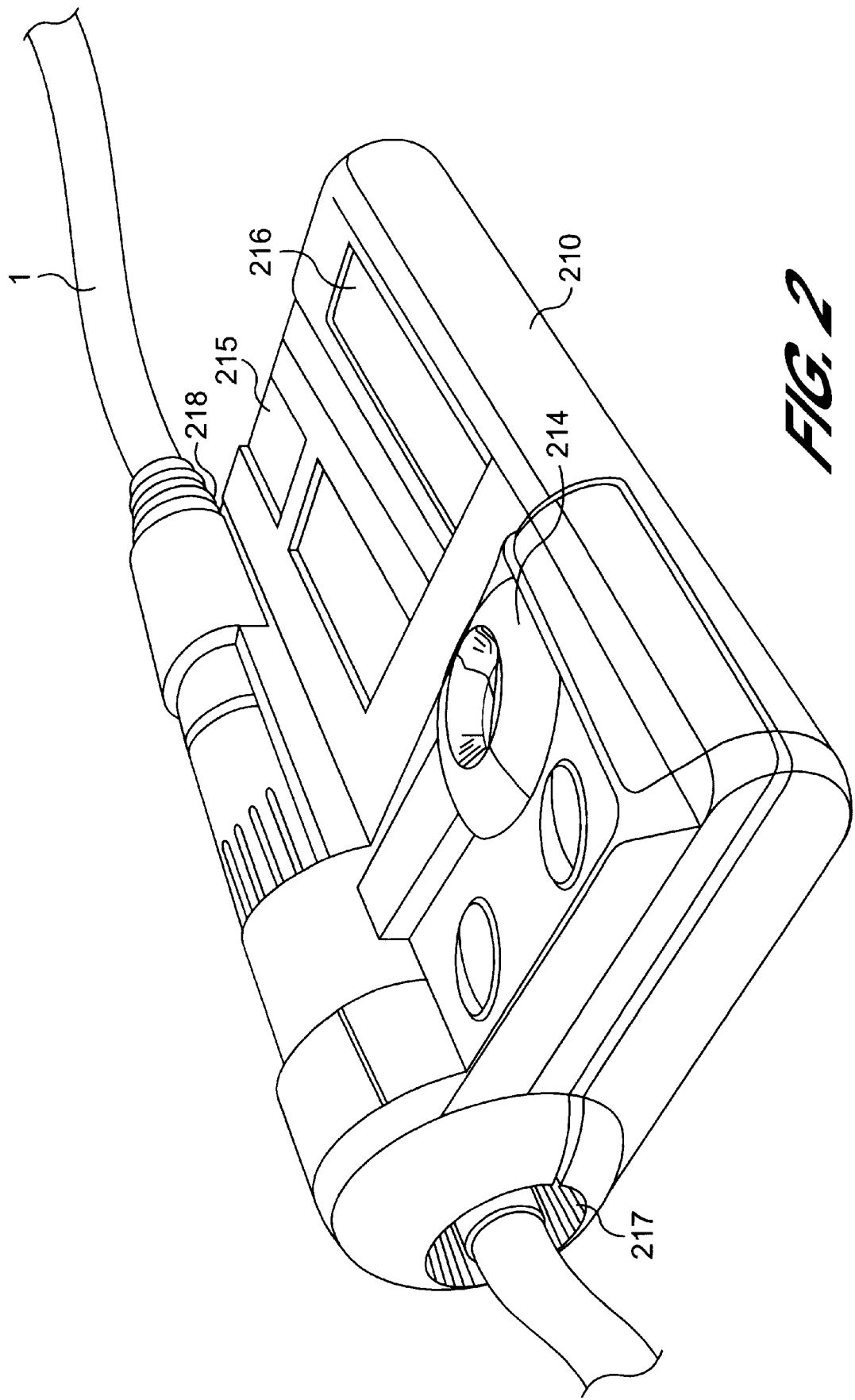
FIG. 2 is a perspective view of the position sensor of FIG. 1.

As the functioning laser assembly of the penetration device is in contact within the vessel tissue, acoustic waves generated by the laser while in contact with the tissue are transmitted through the penetration device 1. The depth sensor 10 is connected to the penetration device 1 as shown in FIG. 1. The depth sensor 10 may be releasably coupled to the penetration assembly 1 through openings in the housing 210, described below. In a preferred form, the sensing assembly 120 is in contact with the penetration assembly 1. The acoustic waves received by the sensing assembly 120 are transmitted to the processing assembly 140. The processing assembly 140 incorporates circuitry which looks for particular acoustic signatures within the sensed acoustic waves that correspond to the penetration of certain tissue or strata within the subject tissue. It is therefore possible to determine the depth of penetration of the device within the subject tissue. The processing assembly 140 preferably includes electronic controls and circuitry that are capable of processing the detected acoustic wave signatures. It is contemplated by the inventor of the present invention that the processing assembly 140 may be part of the control assembly 130.

The present invention is not limited to a position sensor 10 that is in contact with the penetration device; rather, the position sensor may be a remotely operated device that can detect acoustic waves by placement, for example, of the sensing assembly on the abdomen of the patient.

The depth sensor 10 according to the present invention includes a housing 210. The housing 210 includes a hollow interior 211, as shown in FIG. 1. A processing assembly 140 is located within the hollow interior 211. The depth sensor 10 also includes control knobs 212 and 213 located on the housing 210 for monitoring the operation of the depth sensor 10. The depth sensor 10 may be provided with indicators 214, 215 and 216.

The indicators 214, 215, and 216 provide an indication to the user of the position of the penetration device within the tissue wall. The indicators 214, 215, and 216 may comprise audible and/or visual indicator assemblies. Furthermore, the indicators may include also a display screen to indicate the position of the penetration assembly within the vessel.

The housing 210 includes openings 217 and 218 at opposite ends. The penetration assembly 1 extends through the openings 217 and 218 in the housing 310. Located within the housing interior 211 is the sensor assembly 120. The sensing assembly 120 is connected to the processing assembly 130 and control assembly 140 such that information sensed by the sensing assembly 120 may be transmitted to the processing assembly 140 and control assembly 130.

The operation of the depth sensor 10 will now be described. During the repair of the aneurysm, it is necessary to drill through the wall of the vessel to secure a repair graft thereto. The penetration assembly 1 is used to drill through the various layers of the vessel wall. The penetration assembly 1 is in direct contact with the vessel wall during penetration. As the penetration assembly 1 penetrates different layers or strata of the vessel wall, acoustic wave information characteristic of specific tissue penetration layers is generated. Acoustic wave information is generated as the penetration assembly 1 penetrates the repair graft, the intima, media, adventitia and loose connective tissue. Unique acoustic signatures are generated as a result of a change in density within the particular tissue layer as it is heated extremely rapidly during penetration. The acoustic wave information is naturally transmitted along the penetration assembly 1. The sensing assembly 120 is in contact with the penetration assembly 1, as shown in FIG. 1. The acoustic wave information is transmitted from the sensing assembly 120 to the processing assembly 140 and thereafter the control assembly 130. The processing assembly 140 then differentiates the acoustic wave information by comparing it to stored acoustic wave signatures to determine the level of penetration by the penetration assembly 1. The stored acoustic wave signatures were obtained through experimentation and stored in the processing assembly 140. After the processing assembly 140 differentiates the acoustic wave information, the processing assembly 140 transmits a signal to the control assembly 130 indicative of the particular tissue layer. The control assembly 140 may then transmit signals to the indicators 214, 215 and 216 to provide indication to the surgeon performing the repair procedure of the depth of penetration by the penetration assembly 1. For example, a different light may be illuminated to indicate the different depths. Alternatively, a different audible indicator may provide an indication of the sensed depth. It is preferred that a visible or audible indication be provided to the surgeon when transition between the adventitia and loose connective tissue is sensed. The surgeon can then control the depth of penetration of the penetration device in response to the indicators produced by the control assembly 130 through indicators 214, 215 and 216.

With the above-described sensing, it is possible for the surgeon to have a real time indication of the depth of penetration of the vessel wall by the penetration device during the repair procedure. The surgeon may accordingly adjust the pressure applied to the particular tissue or strata being penetrated.

The present invention permits the determination of the penetration of each tissue layer or strata within the vessel wall, which is invaluable to both the surgical procedure and its successful outcome. The depth gauge informs the surgeon when penetration through the adventia to loose connective tissue, has occurred. It will assist in the correct performance of the surgical procedure and aid in the safe and accurate repair of an aneurysm.

It will be apparent to those skilled in the art that various modifications and variations can be made in the construction and configuration of the present invention, without departing from the scope or spirit of the invention. It is intended that the present invention cover the modifications and variations of the invention, provided they come within the scope of the appended claims and their equivalence.

What is claimed is:

1. A depth sensor for sensing a position of a surgical penetration device during a surgical procedure, said depth sensor comprising:

a housing;

connection means for releasably securing said housing to a surgical penetration device;

sensing means for sensing acoustic wave information during the surgical procedure, wherein said sensing means contacts at least a portion of a surgical penetration device located within said housing, wherein said depth sensor senses acoustic wave information transmitted along a penetration device;

processing means for processing said acoustic wave information received by said sensing means; and control means for controlling the operation of the depth sensor based upon information received from said processing means.

2. The depth sensor according to claim 1, wherein said processing means includes means for differentiating the acoustic wave information.

3. The depth sensor according to claim 2, wherein said control means determines the depth of penetration of a surgical penetration device into vessel wall tissue based upon the information generated by said processing means.

4. The depth sensor according to claim 1, wherein said sensing means includes means for detecting acoustic wave information generated as a surgical penetration device penetrates layers of the vessel tissue.

5. The depth sensor according to claim 4, wherein said control means is capable of controlling the depth of penetration of the penetration assembly into a vessel tissue by differentiating the acoustic wave information detected by said detecting means.

6. The depth sensor according to claim 1, further comprising:

indicator means for indicating the position of a surgical device during the surgical procedure.

7. The depth sensor according to claim 6, wherein said indicator means provides an audible indication to a user of the position of the surgical device within a vessel wall.

8. The depth sensor according to claim 6, wherein said indicator means provides a visual indication to a user of the position of a surgical device within vessel wall.

9. The depth sensor according to claim 6, wherein said indicator means operates in response to a signal produced by said control means.

10. A method of measuring the depth of tissue penetration by a penetration device during a surgical procedure, the method comprising the steps of:

securing a depth sensor device to at least a portion of a penetration device;

sensing acoustic wave information using said depth sensor device by sensing acoustic wave information generated during tissue penetration by a penetration device, wherein said depth sensor device senses acoustic wave information transmitted along a penetration device; and processing the acoustic wave information to determine the depth of tissue penetration.

11. The method according to claim 10, wherein said step of processing the acoustic wave information comprises the steps of:

comparing the acoustic wave information with at least one stored acoustic wave signature which corresponds to different tissue level penetration; and producing a signal to provide an indication of the level of penetration based on the comparison of the acoustic wave signature to the at least one stored signature.

* * * * *